(12) United States Patent
Braithwaite et al.

(10) Patent No.: US 6,362,367 B2
(45) Date of Patent: *Mar. 26, 2002

(54) PREPARATION OF ORGANIC ACIDS

(75) Inventors: John Braithwaite, Seabrook, TX (US); David Robert Bryant, South Charleston; David James Miller, Charleston, both of WV (US); John Earl Logsdon, Houston, TX (US)

(73) Assignee: Union Carbide Chemicals & Plastics Technology Corp., Danbury, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/063,675

(22) Filed: Apr. 21, 1998

(51) Int. Cl.$^7$ ................................................. C07C 51/21
(52) U.S. Cl. ....................... 562/531; 562/606; 261/152; 261/147; 261/128; 261/156; 422/200; 422/201; 422/205; 422/208
(58) Field of Search ................ 562/531, 606; 422/201, 200, 205, 228; 261/152, 147, 128, 156

(56) References Cited

U.S. PATENT DOCUMENTS

| | | | |
|---|---|---|---|
| 4,328,175 A | 5/1982 | Roeckel et al. | 261/91 |
| 4,454,077 A | 6/1984 | Litz | 261/91 |
| 4,487,720 A | * 12/1984 | Fruchey | 260/419 |
| 4,544,207 A | 10/1985 | Litz | 299/5 |
| 4,867,918 A | 9/1989 | Kiyonaga et al. | 261/76 |
| 4,900,480 A | 2/1990 | Litz et al. | 261/36.1 |
| 4,919,849 A | 4/1990 | Litz et al. | 261/36.1 |
| 4,965,022 A | 10/1990 | Litz | 261/36.1 |
| 5,009,816 A | 4/1991 | Weise et al. | 261/21 |
| 5,108,662 A | 4/1992 | Litz et al. | 261/16 |
| 5,200,080 A | 4/1993 | Bergman, Jr. et al. | 210/607 |
| 5,356,600 A | 10/1994 | Kiyonaga et al. | 422/234 |
| 5,371,283 A | 12/1994 | Kingsley et al. | 562/416 |
| 5,451,348 A | 9/1995 | Kingsley | 261/36.1 |
| 5,451,349 A | 9/1995 | Kingsley | 261/91 |
| 5,523,474 A | 6/1996 | Kingsley et al. | 562/416 |
| 5,536,875 A | 7/1996 | Roby et al. | 562/412 |

FOREIGN PATENT DOCUMENTS

| | | |
|---|---|---|
| EP | 0 583 509 A1 | 2/1994 |
| EP | 0 781 754 A1 | 7/1997 |
| EP | 0 792 683 A2 | 9/1997 |
| EP | 0 792 865 A1 | 9/1997 |
| EP | 0 796 837 A1 | 9/1997 |

OTHER PUBLICATIONS

Cholette et al., Optimum Performance . . . Conditions, The Can. J. of Chem. Eng. pp. 192–198, Oct. 1961.*

* cited by examiner

Primary Examiner—Rosalynd Keys
(74) Attorney, Agent, or Firm—Marie F. Zuckerman

(57) ABSTRACT

This invention relates to a process for producing one or more organic acids in high purity which process comprises (i) oxidizing in a liquid oxidation reactor one or more organic liquids with essentially pure oxygen or oxygen-enriched air containing at least about 50% oxygen, at a temperature sufficiently stable to prevent cycling of reaction rate, to produce a crude reaction product fluid, and (ii) refining said crude reaction product fluid to give said one or more organic acids in high purity. The oxidation temperature is preferably controlled to within about ±3° C. of a target temperature. The organic acids described herein is useful in a variety of applications, such as intermediates in the manufacture of chemical compounds, pharmaceutical manufacture and the like.

16 Claims, 5 Drawing Sheets

PREPARATION OF ORGANIC ACIDS

BRIEF SUMMARY OF THE INVENTION

1. Technical Field

This invention relates to a process for preparing organic acids by oxidizing in a liquid oxidation reactor an organic liquid with molecular oxygen or a gas containing molecular oxygen to produce an organic acid.

2. Background of the Invention

The manufacture of petrochemicals by the liquid phase oxidation of hydrocarbons with a gaseous oxidant is a very significant commercial operation. Examples of commodity chemicals produced by this process are terephthalic acid, adipic acid, and phenol. Air has traditionally been employed as the gaseous oxidant in such processes, however, it has long been recognized that significant process advantages are offered by using pure oxygen as the oxidant. Such advantages include, for example, improved mass transfer of oxygen into liquid phase because of increased concentration (partial pressure) driving force, improved chemical selectivity resulting from less severe operating conditions, reduced equipment size resulting from reduced gas throughput to the reactor, and reduced waste gas blowoff from the reactor.

However, safety is always a concern when using pure oxygen as the oxidant in any chemical process. There is a continuing need to provide safe and efficient processes for preparing organic acids especially when pure oxygen is used as the oxidant.

3. Disclosure of the Invention

This invention relates to a process for producing one or more organic acids in high purity which process comprises (i) oxidizing in a liquid oxidation reactor one or more organic liquids with essentially pure oxygen or oxygen-enriched air containing at least about 50% oxygen, at a temperature sufficiently stable to prevent cycling of reaction rate, to produce a crude reaction product fluid, and (ii) refining said crude reaction product fluid to give said one or more organic acids in high purity. The oxidation temperature is preferably controlled to within about ±3° C. of a target temperature. By so controlling the oxidation temperature, any temperature upsets will not cause the release of amounts of oxygen to the vapor space of the liquid oxidation reactor which may cause the vapor region to exceed the LOV as defined below.

This invention also relates to a process for producing one or more oxo acids in high purity which process comprises (i) oxidizing in a liquid oxidation reactor one or more oxo aldehydes with essentially pure oxygen or oxygen-enriched air containing at least about 50% oxygen, in which mass transfer between said one or more oxo aldehydes and said essentially pure oxygen or oxygen-enriched air containing at least about 50% oxygen is sufficient to minimize or eliminate byproduct formation, to produce a crude reaction product fluid, and (ii) refining said crude reaction product fluid to give said one or more oxo acids in high purity. By employing a liquid oxidation reactor as described herein, the forced circulation of the reactants, i.e., oxo aldehyde and pure oxygen or oxygen-enriched air containing at least about 50% oxygen, rapidly throughout the liquid oxidation reactor system enhances heat and mass transfer between the reactants, thereby maximizing volumetric reactor productivity and improving desired product selectivity.

This invention further relates to a process for producing one or more organic acids in high purity which process comprises (i) oxidizing in a liquid oxidation reactor one or more organic liquids with essentially pure oxygen or oxygen-enriched air containing at least about 50% oxygen to produce a crude reaction product fluid, and (ii) refining said crude reaction product fluid to give said one or more organic acids in high purity; wherein said liquid oxidation reactor comprises:

a) a vertically positioned tube and shell reactor vessel having a hollow draft tube in the center thereof and heat exchanger tubes in the annular space between the hollow draft tube and the outer wall of the reactor vessel, said reactor vessel having an upper space above and a hollow mixing chamber below said hollow draft tube and said heat exchanger tube;

b) impeller means positioned within said hollow draft tube and adapted to cause the rapid flow of the organic liquid downward through the hollow draft tube into the bottom mixing chamber and rapidly upward through said heat exchanger tubes as a substantially uniform dispersion and into said upper space in the reactor vessel;

c) an upper chamber positioned above and in fluid communication with said reactor vessel, said upper chamber having a vapor space above a desired liquid level;

d) at least one generally horizontal gas containment baffle disposed between said upper chamber and said reaction vessel in such a manner that the vapor space above the liquid level in said upper chamber is maintained below both the LOV and LFL, said gas containment baffle being formed with a central hole to enable said impeller means to extend generally concentrically through said hole in said gas containment baffle;

e) at least one generally horizontal seal baffle disposed within the vapor space of said upper chamber in such a manner that the vapor space above said seal baffle is maintained under an inert atmosphere, said seal baffle being formed with a central hole to enable said impeller means to extend generally concentrically through said hole in said seal baffle;

f) conduit means for introducing said organic liquid into the reactor vessel and for introducing said pure oxygen or oxygen-enriched air containing at least about 50% oxygen into said reactor vessel or the upper chamber for rapid recirculation with the organic liquid downward through the hollow draft tubes into the bottom mixing chamber and rapidly upward through said heat exchanger tubes into said upper space;

g) conduit means for withdrawing product liquid from the reactor vessel;

h) conduit means for flowing cooling fluid to the reactor vessel for the removal of exothermic heat of reaction generated within said reactor vessel; and i) control means for maintaining a desired liquid level within the reactor vessel or within the upper chamber. By installing a baffle in the upper chamber, any equipment or parts having the potential to generate frictional heat, e.g., a seal through which the agitator shaft passes into the liquid oxidation reactor, will not pose an ignition hazard if oxygen and organic vapors are prevented from contacting such equipment or parts in an upset condition such as loss of agitation in the reaction zone.

This invention yet further relates to a process for producing one or more organic acids in high purity which process comprises (i) oxidizing in a primary liquid oxidation reactor one or more organic liquids with essentially pure oxygen or oxygen-enriched air containing at least about 50% oxygen to produce a first crude reaction product fluid, (ii) removing said first crude reaction product fluid from said primary liquid oxidation reactor, (iii) feeding said first crude reaction product fluid to at least one secondary liquid oxidation reactor or plug flow reactor, (iv) oxidizing in said secondary liquid oxidation reactor or plug flow reactor said first crude reaction product fluid with essentially pure oxygen or oxygen-enriched air containing at least about 50% oxygen to produce a second crude reaction product fluid, and (v) refining said second crude reaction product fluid to give said one or more organic acids in high purity. By configuring two or more liquid oxidation reactors in series or a liquid oxidation reactor followed in series by a plug flow reactor, efficiency can be improved by increasing conversion of the organic liquid.

DETAILED DESCRIPTION

Figure 1:
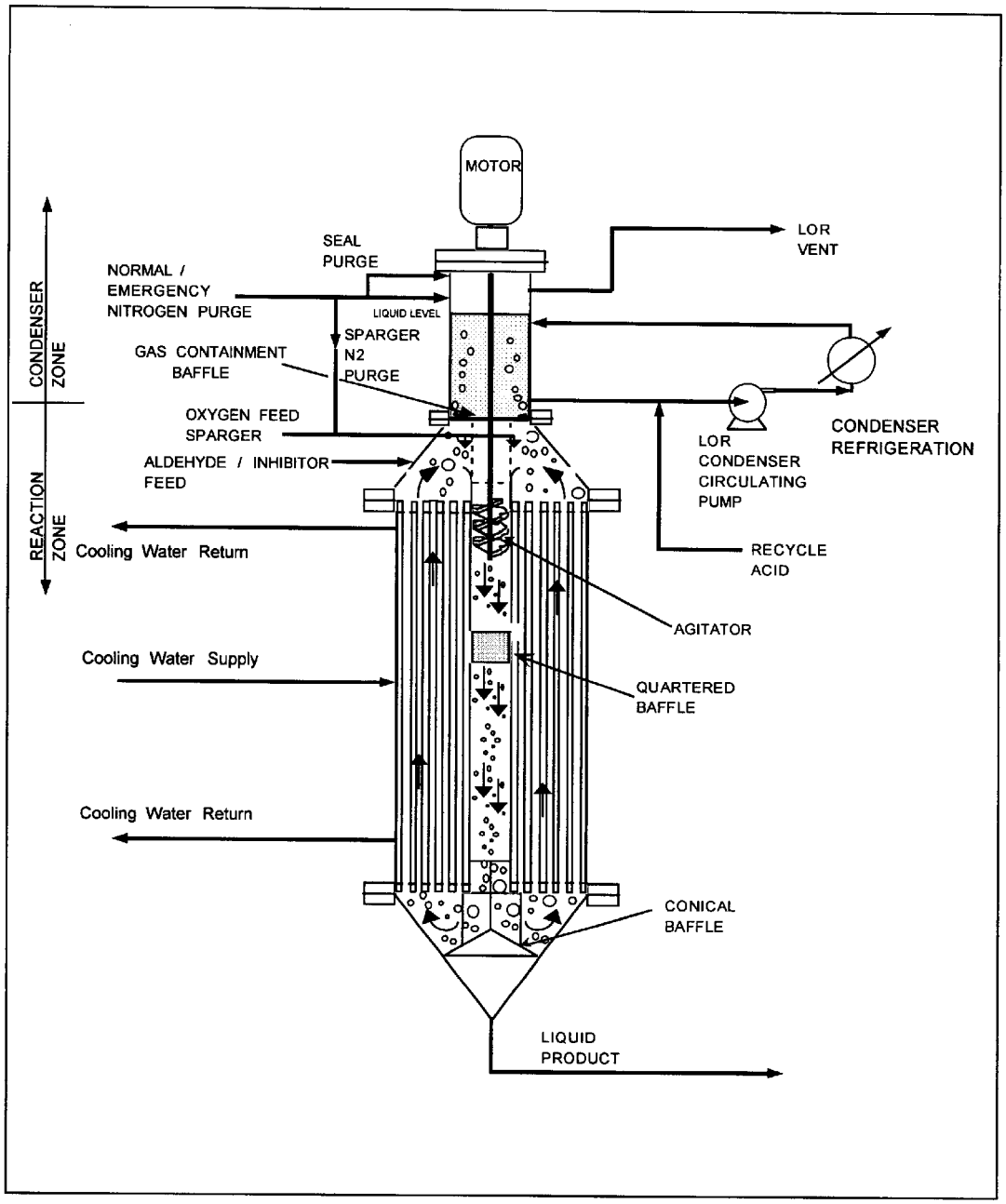
FIG. 1 is a schematic of a liquid oxidation reactor.

As used herein, the following abbreviations have the indicated meanings: Lower Flammable Limit (LFL)—a composition below which a mixture contains insufficient fuel to support combustion; Upper Flammable Limit (UFL)—a composition above which a mixture contains too much fuel to support combustion; and Limiting Oxygen Value or Concentration (LOV or LOC)—the oxygen content below which a mixture will not support combustion irrespective of other component composition.

Liquid phase oxidation can be described as a two-step operation involving (i) inter-phase mass transfer of oxygen into the liquid phase; and (ii) chemical reaction of dissolved oxygen and hydrocarbon in the liquid phase via a free radical mechanism.

The overall rate of oxidation is a function of both physical transport phenomena and of the chemical reaction velocity. The transfer of oxygen from gas to liquid phase is a critical aspect of the process and is often the rate limiting step since the solubility of oxygen in many hydrocarbon systems is inherently low. Gas to liquid mass transfer is improved by increasing the interfacial contact area between the phases. In chemical reactors this is typically achieved by introducing the gas via a submerged sparger designed to generate gas bubbles and by promoting bubble dispersion and break-up through use of mechanical agitation. The liquid oxidation reactor has been designed with both a high degree of gas dispersion and gas-liquid mixing to promote oxygen transfer into the liquid phase and minimize the chemical selectivity losses due to mass transfer deficiencies.

Chemical reaction rate is influenced by reaction temperature and raw material concentrations. Reactions with a low activation energy are not temperature sensitive, however, those with a high activation energy can exhibit significant rate changes for only minor temperature changes. For strongly exothermic reactions such as oxidations, this temperature sensitivity is acute because a temperature deviation which effects the reaction rate also impacts the heat evolution rate. As an illustration, a small downward deviation in oxidation temperature which causes a reduction in reaction rate correspondingly reduces the heat evolution rate, which in-turn can result in a further reduction in reaction temperature and reaction rate. The net result can be a pronounced instability in reaction rate control.

For oxidation processes, reaction instability can have serious safety consequences because oxidation reactors maintain strict safety controls over the allowable oxygen concentration in the blowoff gas in order to maintain the blowoff gas below the LOC. For reasons of improved mass transfer, oxidation processes are typically operated within a window where the level of oxygen breakthrough is maximized under the LOC limit. Therefore reaction rate stability is of critical importance because variations in reaction rate swing the level of unreacted oxygen breakthrough into the blowoff gas. These upsets can force the process to operate well below the LOC limit so as to prevent upward perturbations in oxygen concentration exceeding the LOC level.

For this reason commercial oxidation reactors often purposefully operate in a regime where transport phenomena dominate the rate and the chemical selectivity advantages of oxidation free from mass transfer limitations are traded-off for improved stability.

Organic liquids which may be employed in the process of this invention include, for example, aldehydes, alcohols, alkylbenzenes, cyclic aliphatic hydrocarbons and the like. Illustrative aldehydes include, for example, formaldehyde, acetaldehyde, propionaldehyde, n-butyraldehyde, 2-methylbutyraldehyde, iso-butyraldehyde, n-valeraldehyde, caproaldehyde, heptaldehyde, nonylaldehyde, phenylacetaldehyde, benzaldehyde, o-tolualdehyde, m-tolualdehyde, p-tolualdehyde, salicylaldehyde, p-hydroxybenzaldehyde, anisaldehyde, vanillin, piperonal, 2-ethylhexaldehyde, 2-propylheptaldehyde, 2-phenylpropionaldehyde, 2-[p-isobutylphenyl]propionaldehyde, 2-[6-methoxy-2-naphthyl] propionaldehyde and the like. Illustrative alcohols include, for example, 2-ethylhexanol, 2-propylheptanol, isobutyl alcohol, 2-methyl-1-butanol, and the like. Illustrative alkylbenzenes include, for example, p-nitrotoluene, o-bromotoluene, ethylbenzene, n-butylbenzene, m-xylene, p-xylene, toluene and the like. Illustrative cyclic aliphatic hydrocarbons include, for example, cyclohexane, cyclooctane, cycloheptane, methylcyclohexane and the like. Illustrative of suitable organic liquids include those permissible starting material liquids which are described in Kirk-Othmer, Encyclopedia of Chemical Technology, Third Edition, 1984, the pertinent portions of which are incorporated herein by reference.

Preferred organic liquids include aldehydes, particularly aldehydes prepared by hydroformylation processes such as disclosed, for example, in U.S. Pat. Nos. 3,527,809, 4,148,830, 4,247,486, 4,593,127, 4,599,206, 4,668,651, 4,717,775 and 4,748,261. Such aldehydes prepared by hydroformylation processes are referred to herein as "oxo aldehydes".

The oxidizing agent useful in the process of this invention is pure oxygen or oxygen-enriched air containing at least about 50% oxygen. The oxygen-enriched air may contain, for example, inert gases such as nitrogen, carbon dioxide or noble gases. The preferred oxidizing agent is pure oxygen. Such oxidizing agents can be used in amounts described below and in accordance with conventional methods.

The oxidizing agent is employed in an amount sufficient to permit complete oxidation of the organic liquid, e.g., aldehyde. Preferably, the oxidizing agent is added at a rate, e.g., oxygen partial pressure, sufficient to suppress or eliminate side reactions of the organic liquid such as decarbonylation of the aldehyde, and more preferably, an oxygen partial pressure of from about 1 psi or less to about 200 psi or greater.

The oxidation step of the process of this invention may be conducted at a reaction pressure from about 50 to about 150 psig. The preferred operating pressure is from about 70 to about 120 psig. The liquid oxidation reactor preferably operates at a pressure of about 100 psig, and preferably may be confined within a pressure range of about 80 to about 115 psig by high and low pressure automatic shutdown limits.

For aldehyde oxidations, it has been observed that aldehyde decarbonylation side reaction to $C_1$ and $C_{n-1}$ fragments is very low at oxygen partial pressures above 40 psig, but increases exponentially at oxygen partial pressures below 40 psig, presumably due to the increasingly acute impact of oxygen mass transfer limitations. Other process conditions were consistent with commercial operating conditions (temperature 65° C., reaction rate <15 gmol/lit/hr). Therefore, for aldehyde oxidations, the operating pressure for the liquid oxidation reactor should preferably be above about 40 psig to maximize selectivity to the organic acid product.

The upper limit on reaction pressure is fixed by considerations of vessel wall thickness. A deflagration occurring in the liquid oxidation reactor vapor space will cause a pressure spike to approximately 10 times initial pressure. Designing the vessel wall thickness to contain the pressure run-up from a potential deflagration limits the normal operating pressure.

The oxidation step of the process of this invention may be conducted at a reaction temperature from about −25° C. or lower to about 125° C. Lower reaction temperatures may generally tend to minimize byproduct formation. In general, oxidations at reaction temperatures of about −10° C. to about 100° C. are preferred.

The focus of this invention is on temperature control of a kinetically controlled oxidation reaction thereby allowing improved product quality. This invention recognizes and addresses the impact of temperature on oxygen concentration in the liquid oxidation reactor vapor space. By controlling a temperature sensitive oxidation reaction in a region which is not subject to mass transfer limitations, improved product quality can result because of reduced byproduct formation. Operation of the reaction requires close control of reaction temperature since operation of a highly exothermic reaction with a high activation energy in a kinetically controlled regime can make the reaction extremely temperature sensitive. Temperature sensitivity can cause fluctuations in the oxygen breakthrough into the reactor vapor space.

Particularly, if organic liquid A is oxidized in a liquid oxidation reactor to organic acid B in the following manner:

$$xA + yO_2 = zB$$

wherein x, y, and z are stoichiometric constants, then the rate of oxidation of organic liquid A is given by an expression of the form:

$$r_A = k * A_1 * e^{\frac{-E}{RT}} * C_A^n * P_{O2}^m$$

wherein $r_A$ is reaction rate of A; k, n, m are constants, $A_1$ is Arrhenius constant, E is activation energy, T is absolute temperature, R is universal gas constant, $C_A$ is concentration of organic liquid A, and $P_{O2}$ is oxygen partial pressure.

If the reaction temperature changes by a small increment from $T_1$ to $T_2$ the change in reaction rate, $\Delta r_A$, can be calculated as follows:

$$\Delta r_A = k * A_1 * \left[ e^{\frac{-E}{RT_1}} - e^{\frac{-E}{RT_2}} \right] * C_A^n * P_{O2}^m$$

The impact on oxygen consumption rate is:

$$\Delta F_{O2} = \Delta r_A * V * y/x$$

where V is the reaction zone volume.

A downward temperature change will cause a reduction in oxygen consumption rate. If the oxygen feed rate to the reaction zone is not reduced the purge rate of oxygen ($F_{O2}$) across the gas baffle will increase until it is equal to:

$$(F_{O2})_2 = (F_{O2})_1 + \Delta F_{O2}$$

wherein $(F_{O2})_1$ is the initial purge rate of oxygen across the gas baffle. Neglecting organic flux into the vapor space, the concentration of oxygen ($C_{O2}$) in the vapor space above the condenser liquid level will equal:

$$C_{O2} = \frac{(F_{O2})_2}{N_2 + (F_{O2})_2}$$

wherein $N_2$ is the nitrogen purge rate through the vapor space.

The following limit must be applied to maintain the vapor space in a safe operating region:

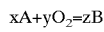

$$C_{O2} < \text{System LOC}$$

It follows that the liquid oxidation reactor reaction zone temperature controller must be capable of maintaining the reaction temperature within a range where temperature upsets do not cause the process to release amounts of oxygen to the vapor space which cause the vapor region to exceed the LOC. This limit is within ±3° C., preferably ±2° C., and more preferably ±1° C., of the target temperature for oxidation reactions at preferred rates of nitrogen purge through the vapor space. The target temperature is selected from a temperature ranging from about −25° C. or lower to about 125° C., preferably from about −10° C. to about 100° C. Such temperature upsets can cause cycling of reaction rate. Cycling refers to frequent periodic and extreme changes in reaction rate during the oxidation process. Cycling conditions disrupt steady operation of the unit. Uniform temperature is required to eliminate cycling of reaction rate.

Figure 3:
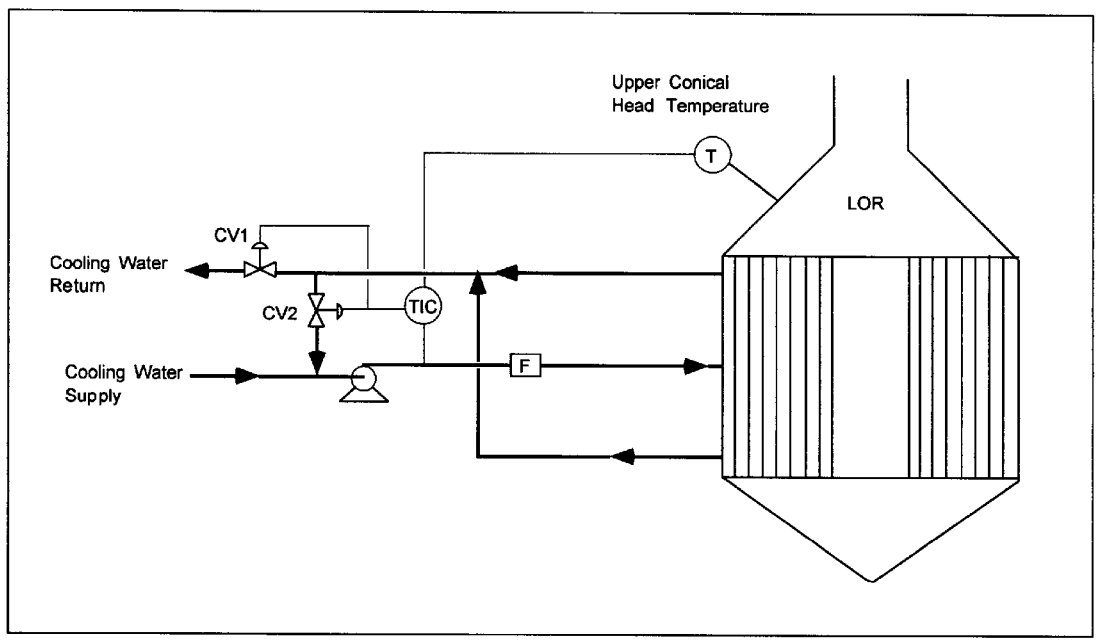
FIG. 3 depicts a temperature control mechanism for a liquid oxidation reactor.

The liquid oxidation reactor should be provided with a temperature control loop sufficient for maintaining or controlling reaction zone temperature within the above stated limits. An illustrative design employs the strategy shown in FIG. 3. In this scheme the upper conical head temperature is controlled by adjusting the cycle water inlet temperature. The cycle water inlet temperature is controlled by manipulating the quantity of cycle water which is recycled from the shell return line to the shell inlet using valves CV1 and CV2. These two motor valves have a V-groove flow area which provides a highly linear flow response to demand changes. Preferably, the upper conical head temperature is controlled to within ±0.5° C. thereby providing desired stability and an acceptable variation in the level of oxygen breakthrough in the vapor space. The significance of this invention is that tight control of reaction temperature is needed by the liquid oxidation reactor for reasons of stability and to capitalize upon the process advantages of operating in a chemical rate controlled region. The actual means of achieving temperature control may be subject to several design variations. In a preferred embodiment for aldehyde oxidation, a temperature control within ±1° C. of a target reaction temperature for oxidations conducted in the liquid oxidation reactor having an activation energy of greater than 15 kcal/mol and exothermic heat of reaction of greater than 100,000 BTU/lb-mol is desired.

The oxidation step of the process of this invention is conducted for a period of time sufficient to produce an organic acid. The exact reaction time employed is dependent, in part, upon factors such as temperature, nature and proportion of starting materials, and the like. The reaction time will normally be within the range of from about one-half to about 200 hours or more, and preferably from less than about one to about 10 hours.

The oxidation step in the process of this invention can be carried out in the liquid state and can involve a batch or continuous liquid recycle system.

The oxidation step of the process of this invention may be conducted in the presence of an organic solvent. Depending on the particular promoter and reactants employed, suitable organic solvents include, for example, alcohols, alkanes, esters, acids, amides, aromatics and the like. Any suitable solvent which does not unduly adversely interfere with the intended oxidation process can be employed and such solvents may include those heretofore commonly employed in known processes. Mixtures of one or more different solvents may be employed if desired. Solvents which partially or totally dissolve the aldehyde and do not react with peracids may be useful. The amount of solvent employed is not critical to this invention and need only be that amount sufficient to provide the reaction medium with the particular substrate and product concentration desired for a given process. In general, the amount of solvent when employed may range from about 5 percent by weight up to about 95 percent by weight or more based on the total weight of the reaction medium.

In a preferred embodiment, when the requisite aldehyde product is provided by a hydroformylation reaction, suitable solutions can be provided by using liquid aldehydes or by melting solid aldehydes. However, suitable solutions may consist of the aldehydes dissolved in an appropriate solvent (e.g., in the solvent in which the first step of the process of this invention was conducted). Any solvent which will dissolve the aldehyde product and is unreactive with pure oxygen or oxygen-enriched air containing at least about 50% oxygen may be used. Examples of suitable solvents are ketones (e.g., acetone), esters (e.g., ethyl acetate), hydrocarbons (e.g., toluene) and nitrohydrocarbons (e.g., nitrobenzene). A mixture of two or more solvents can be employed to maximize the purity and yield of the desired aldehyde. The solution used may also contain materials present in the crude reaction product of the aldehyde-forming reaction (e.g., catalyst, ligand and heavies). Preferably, however, the solution consists essentially of only the aldehyde and the solvent. The concentration of the aldehyde in the solvent solution will be limited by the solubility of the aldehyde in the solvent.

In an embodiment of this invention, aldehyde oxidation occurs through a complex free radical mechanism. This process can be simplified into 2 basic steps represented by (i) formation of a peroxy acid from a mol of aldehyde, and (ii) reaction of the peroxy acid with an additional mol of aldehyde to yield 2 mols of acid product.

Step (1) is believed to occur by a free radical mechanism which can be represented by:

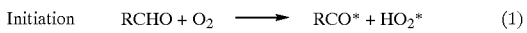
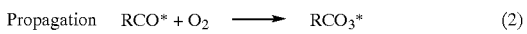
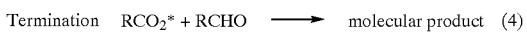

The initiation step involves the production of an acyl radical (RCO˙) from the reaction of aldehyde with oxygen. No external promoter is employed to generate free radicals, instead the mechanism of generation is believed to involve decomposition of peroxides either thermally, or, catalyzed by metal surfaces. However, other initiations may employ a promoter such as a cobalt or manganese salt.

During the chain propagation step, the acyl radical reacts rapidly with oxygen to form a peroxyacyl radical ($RCO_3$˙), which, in a subsequent slower step, reacts with a mol of aldehyde to form a peroxy acid and a new acyl radical. This propagation reaction proceeds until the chain is terminated after a large number of cycles by the formation of non-radical products.

In step (2) the peroxy acid reacts with an additional mol of the starting aldehyde to form a peroxy acid-aldehyde adduct, which then decomposes to form 2 mols of the product acid.

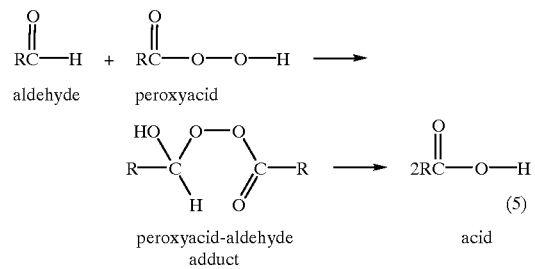

There are several side-reactions to unwanted byproducts which compete with the above mechanism. Under conditions of poor mass transfer of oxygen into the liquid phase, the acyl radical involved in reaction 2 above may decompose as follows:

The remaining radical, R, contains one less carbon than the initial acyl radical and may undergo further oxidation to produce an aldehyde or alcohol. In the case of valeraldehyde oxidation, butyraldehyde or butanol may result from this pathway. The extent of carbon monoxide generation, and the rate of formation of compounds containing one less carbon atom (n−1) than the feedstock hydrocarbon, are thus measures of the degree of oxygen starvation present at the reaction conditions.

The formation of $C_{n-1}$ components can impact product refining if they, or components formed by subsequent oxidation reactions, have a close volatility to the desired product. For example, valeraldehyde oxidation to valeric acid may produce small quantities of butyraldehyde and butanol as unwanted byproducts of the oxygen starved mechanism described above. Butyraldehyde may undergo yet a further oxidation to yield butyric acid, and butanol may esterify with valeric acid to yield butyl valerate. Both butyric acid and butyl valerate are difficult to separate from valeric acid in conventional refining columns because they are close boiling.

Figure 5:
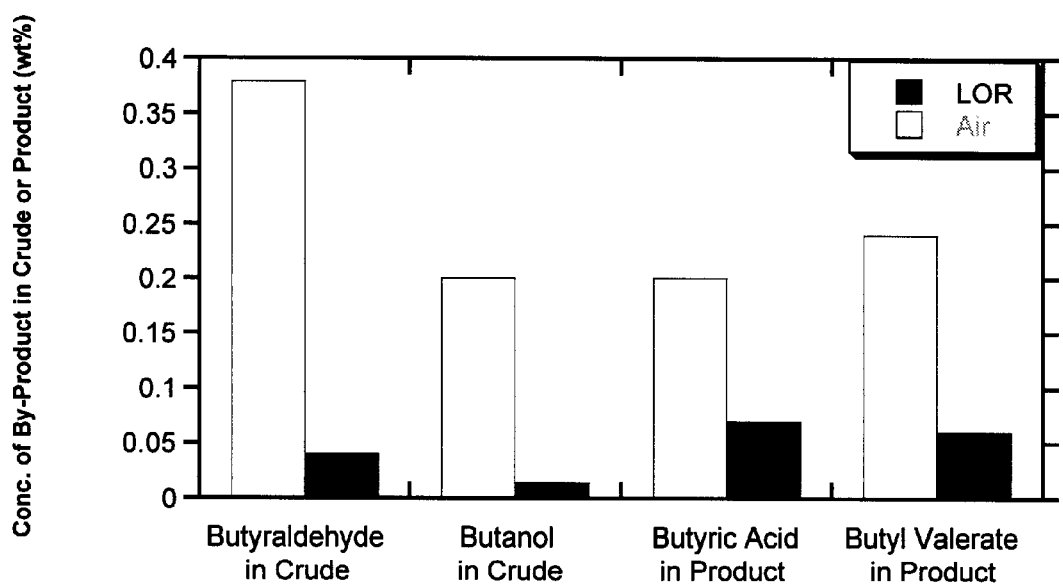
FIG. 5 shows a comparison of byproduct levels in crude and refined product produced by air converters and the liquid oxidation reactor.

The relative amounts of butyraldehyde and butanol present in crude oxidizer product are compared in FIG. 5 for the liquid oxidation reactor and an air converter. After refining in similar fractionation processes, the quantities of butyric acid and butyl valerate remaining in the refined valeric acid are also shown in FIG. 5. The reduction in butyric acid and butyl valerate correspond to quantitative improvements in valeric acid purity.

As indicated above, the organic acid-forming process of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

As indicated above, the oxidation process of this invention is accomplished by the use of pure or nearly pure oxygen as the feed gas in the place of feed air and by the carrying out of the oxidation reaction in a liquid organic reaction system in place of a conventional reaction system. The reactor technology described herein provides an advantaged and safe means of conducting liquid phase oxidations with pure oxygen. This technology is referred to as the liquid oxidation reactor technology.

A schematic diagram of liquid oxidation reactor technology is shown in FIG. 1. The liquid oxidation reactor consists of two discrete process zones partitioned by a gas containment baffle. Below the gas containment baffle is a well mixed reaction region in which organic liquid oxidation occurs. Above the gas containment baffle is a condenser region in which blowoff gases are treated before exiting the reactor.

The reaction zone comprises a vertical shell and tube heat exchanger with upper and lower conical heads mounted at either end of the tube sheets. Located in the center of the tube bundle is a cylindrical draft tube containing a downward pumping helical-screw impeller. Oxygen and organic liquid, e.g., aldehyde, are fed into the upper conical head near the impeller suction. Oxygen is introduced through two spargers mounted either side of the impeller shaft, organic liquid through an open pipe at the vessel wall.

The impeller dissipates oxygen feed as a fine dispersion of gas bubbles and pumps the resultant two phase mixture downwards through the draft tube and into the lower conical head. Three cross-shaped (quadrant) baffles located respectively at the draft tube suction mouth, below the impeller, and in the draft tube exit, ensure efficient axial draft tube pumping by minimizing rotational swirl. Fluid exiting the draft tube enters the lower conical head where a conical baffle projected at the draft tube creates a roll wave in which turbulent recirculation occurs before fluids are returned to the upper conical head through the tube bundle. Heat of reaction is removed by a shell side coolant.

The reaction zone is operated liquid full and a liquid level is maintained in the condenser head above the gas containment baffle by controlling the rate at which liquid product is withdrawn from the base of the reaction zone. Crude liquid product is removed in an ungassed form from beneath a lower conical shaped baffle. Gas-liquid phase separation is achieved by withdrawing product through a narrow outer circumferential drainage slit in the conical baffle at a sufficiently low rate to allow buoyancy forces to disengage gas bubbles from the liquid product.

The function of the gas containment baffle is to ensure high levels of oxygen consumption in the reaction zone by re-circulating unreacted oxygen evolving from the top tubesheet back into the draft tube. The baffle consists of a solid metal plate with a small de-gassing slit located near the outer circumference. A small purge of gas has to be vented from the reaction zone into the condenser head through the de-gassing slit in order to prevent the accumulation of inert gases formed as a byproduct of aldehyde oxidation. The design intent of the baffle is attain an oxygen consumption efficiency greater than 97.5%. This is achieved by limiting the vent rate of gas through the de-gassing slit to a level which as closely as possible balances the production rate of gaseous reaction byproducts. The gas containment baffle preferably has a steady bearing which comprises a split ring bushing mounted around the impeller shaft and supported on the gas containment baffle. The function of the steady bearing is to minimize lateral movement of the impeller shaft which may cause metal to metal impingement of the outer tip of the impeller blades and inner wall of the draft tube.

Above the gas baffle is located a direct contact condenser head. The function of the condenser is to remove condensable organic vapors from the blowoff gas and thereby ensure that the blowoff gas composition is below the LFL. To achieve this, the condenser liquid temperature is controlled at approximately −5 to 25° C., depending on the system organic vapor pressure, by externally circulating process liquid through the evaporator of a refrigeration unit. To assist in ensuring the blowoff gas is fuel lean, a small recycle stream of acid is recirculated from the refining process and added to the condenser circulation loop. The purpose of this stream is to provide a localized high concentration of low volatility acid above the gas containment baffle.

Above the condenser liquid level, a continuous purge of nitrogen is added to the vapor space to dilute unreacted oxygen to a level well below the LOV. Redundant oxygen analyzers continuously monitor the vapor space to ensure the blowoff oxygen is at safe levels. The nitrogen purge also serves to sweep the vapor space into a vent collection header. A reactor pressure of 50–150 psig is maintained by controlling the vent rate of the blowoff gas.

Figure 4:
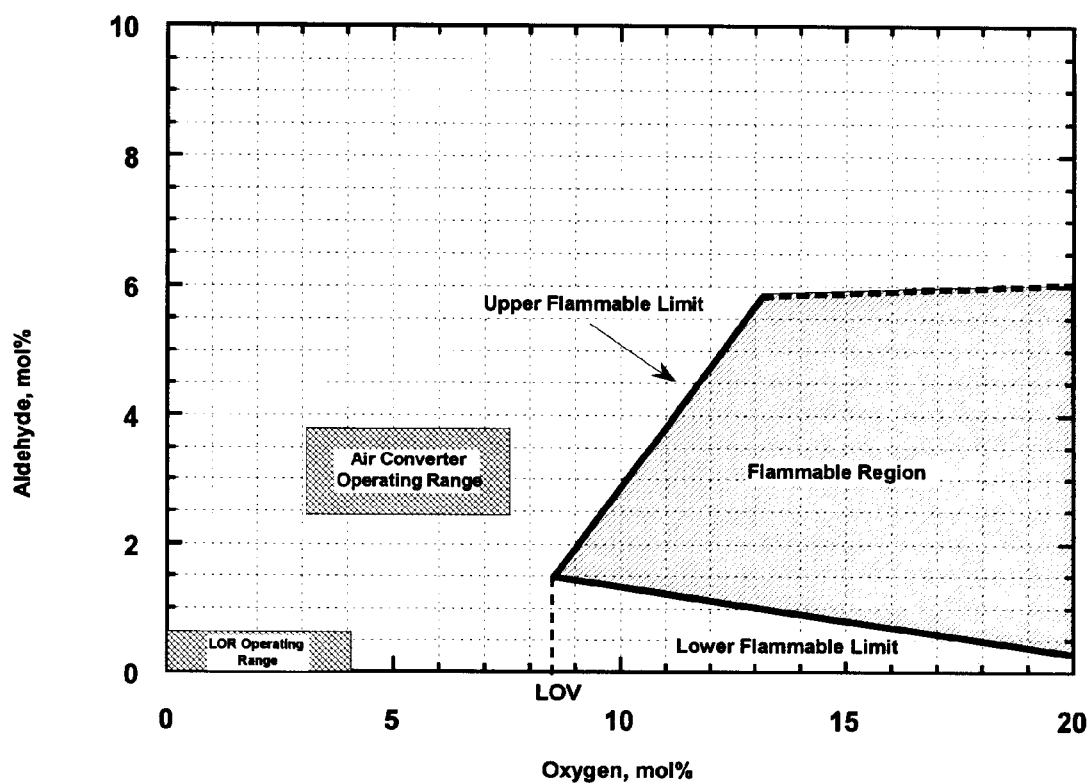
FIG. 4 illustrates a comparison of blowoff vapor composition for liquid oxidation reactor and air converters with flammable range. The liquid oxidation reactor operates below both the LFL and LOV while the air converters operate below only the LOV.

In conventional air-based liquid oxidation reactor technologies, air flow is in a single pass upwards through the reactor and the blowoff gas is maintained below the LOV by limiting the feed rate of oxidant. This can cause undesirable mass transfer consequences due to oxygen deficiency in the liquid phase, especially in the upper portion of the reactor where the oxygen concentration is lowest. In addition, the blowoff gas is typically in thermal equilibrium with the liquid phase at the oxidation temperature, which causes the blowoff gas to be above the LFL for most volatile organic systems. In the liquid oxidation reactor, the combination of condenser cooling, recycle acid addition, and nitrogen purge, secures the blowoff composition well away from the flammable region while allowing the reaction zone to operate advantageously at oxygen partial pressures far in excess of conventional oxidation technologies. This is shown graphically in FIG. 4 for valeraldehyde oxidation.

Figure 2:
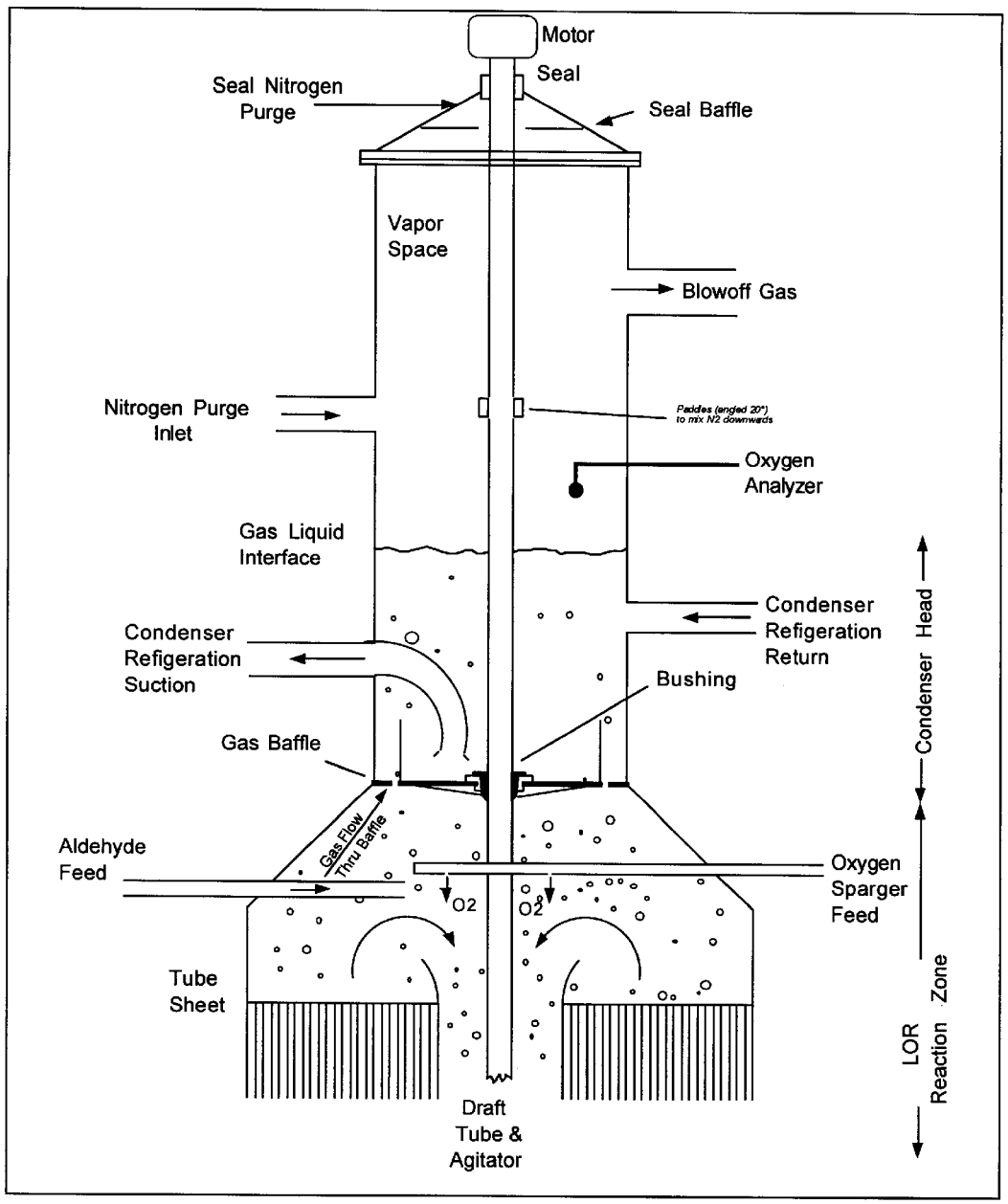
FIG. 2 depicts the condenser head of a liquid oxidation reactor.

Details of the upper portion of an liquid oxidation reactor employed for aldehyde oxidation are shown in FIG. 2. Under normal operation conditions, the composition of the vapor space is maintained below both the LOC and the LFL. Additionally no ignition source is present.

If mechanical agitation in the liquid oxidation reactor reaction zone is lost because of an equipment malfunction or power loss, the oxygen gas dispersed in the reaction zone will rise by buoyancy through the gas baffle and enter the vapor space of the liquid oxidation reactor. To prevent flammable conditions in the vapor space, the normal nitrogen purge through the vapor space is automatically increased by the reactor shutdown system to a level which will dilute the oxygen content below the LOC.

The agitator shaft passes into the liquid oxidation reactor vessel through a mechanical seal shown in FIG. 2. The seal is cooled by condensate and under normal operating conditions presents no ignition hazard to the vapor space. It is however conceivable that a mechanical failure of the seal may create a scenario where sufficient frictional heat is generated by the seal to pose an ignition hazard.

The seal cannot pose an ignition hazard if oxygen and organic vapors are prevented from contacting the seal in an upset condition such as loss of agitation in the reaction zone. One means of achieving this is to place a baffle comprising a flat metal plate immediately under the seal. The baffle is sealed to the vessel wall and contains a circular hole in its center sufficient to accommodate the agitator shaft with a small annular clearance of about 0.5" between the shaft face and the outer tip of the baffle plate. A dedicated nitrogen purge is then introduced above the baffle at a flowrate which is sized to cause a slight pressure increase above the baffle in relationship to the vapor space pressure below the seal baffle. Nitrogen is thus forced to pass in a downward motion away from the seal through the annular clearance space between the shaft and the baffle outer tip with no upward mixing of gas from the bulk vapor space. In this way a secure inert blanket around the seal is achieved.

The vapor space of the liquid oxidation reactor is normally operated under non-flammable conditions. However multiple equipment failures, such as those which cause the agitator to cease providing gas dispersion to the reaction zone, can cause the vapor space to become flammable. Under these conditions it is important to ensure that no vapor space ignition source exists. A conceivable ignition source may be generated by a mechanical failure of the seal through which the agitator shaft passes into the vapor space. Such a seal failure may deform the seal faces and generate frictional heat sufficient to ignite flammable gases which come into contact with the point of failure. The seal baffle ensures no flammable gases contact the seal.

If ignition of the vapor space occurs, a deflagration explosion will result. This event involves the propagation of a flame front through the vessel at less than the speed of sound and an associated pressure wave which can approach 10 times the initial pressure. If sufficient run length and turbulent mixing is available in the vapor space, a deflagration wave can run up to and transition into a detonation explosion. A detonation is a much more powerful event than a deflagration and generates a pressure shock wave traveling at greater than the speed of sound. The liquid oxidation reactor vessel wall thickness can be designed to contain the peak pressure resulting from a deflagration without loss of vessel integrity. A detonation is too powerful to contain with any reasonable wall thickness and will likely result in loss of vessel containment and shrapnel.

A characteristic minimum cell diameter and critical path length required to transition a deflagration to a detonation has been defined in the literature for a limited number of hydrocarbon systems. These values are sensitive to the specific geometry of the test apparatus and do not transfer to scale-up scenarios with good accuracy. It is therefore difficult to obtain definitive design data on the limiting cell size and run-up length required to transition a deflagration into a detonation in the liquid oxidation reactor. The volume of vapor space in a liquid oxidation reactor may be sufficiently large to place the liquid oxidation reactor in a gray area where additional explosion protection must be considered since the potential for a deflagration roll-over to a detonation may be considered unlikely but uncertain. The seal baffle by providing further security against vapor phase ignition is an important safety feature of liquid oxidation reactors where the vapor volume is large enough that the possibility of a deflagration-detonation transition occurring cannot be conclusively ruled out.

In the oxidation of organic liquids, it is necessary to prevent a potentially explosive or flammable vapor-gas phase mixture from developing in the overhead gas phase. If the concentration and volume of organics in the vapor space cannot be adequately controlled, then the TNT equivalents may exceed safe operation of the reactor vessel and thereby pose a serious safety concern. A liquid oxidation reactor process and system as disclosed in U.S. Pat. No. 4,900,480 has been found to be advantageous for such organic liquid oxidation applications.

By replacing air with oxygen, the partial pressure of oxygen containing gas bubbles within the oxidation reactor is significantly greater than the inherently limited oxygen partial pressure in air. Consequently, the driving force for mass transfer is greater, and the likelihood of oxygen starved conditions, which cause byproduct formation is lower.

The liquid oxidation reactor system is a well mixed stirred reactor system, with oxygen bubbles uniformly distributed throughout the reactant liquid. The liquid oxidation reactor approach, in its most common embodiment, uses a mixing impeller and draft tube arranged to disperse and circulate gas bubbles in the liquid phase. When used to safely react gaseous oxygen with flammable liquids, the gas bubbles comprise a mixture of feed oxygen, flammable organic vapor and byproduct gases. With the gas bubbles dispersed as small bubbles throughout the liquid phase, the flammability hazard associated with the oxygen and the organic vapor mixture is mitigated by the heat capacity of the surrounding liquid, which adsorbs the heat or reaction in the event of bubble ignition, and because the flame from a single bubble cannot propagate through the liquid phase.

In the liquid oxidation reactor system as disclosed in U.S. Pat. No. 4,900,480, a recirculating liquid reaction zone is separated from, but remains in fluid communication with, a quiescent zone that is in contact with the overhead gas phase. A baffle between said zones serves to substantially prevent gas bubbles that are carried with the liquid in the recirculating liquid zone from disengaging the liquid because of their buoyancy, thus insuring that the bubbles are recirculated with the liquid and are efficiently consumed by reaction. Any gas bubbles that do escape from the recirculating liquid zone under the baffle, and pass upward through the quiescent zone, are collected in the gas space above the quiescent zone, where they are rendered non-flammable by the addition of inert gas, e.g. nitrogen, to said gas space.

Since the liquid oxidation reactor system is a well mixed stirred tank reaction system, oxygen bubbles are generally uniformly distributed throughout the liquid. Thus, in the operation of the liquid oxidation reactor system in the practice of this invention, there are essentially no zones in the reactor that are oxygen starved due to poor gas-liquid contacting. Depending on the vapor pressure of the liquid, which acts as a diluent, the average oxygen concentration in the gas bubble is much higher in an liquid oxidation reactor system than it is in a conventional reactor. In liquid oxidation reactor systems with a very low liquid vapor pressure, the average oxygen concentration can approach 95% or higher. This compares favorably to the average 5% oxygen concentration in a conventional air based stirred tank reactor and to the average of about 13% in an air based bubble column reactor.

For aldehyde oxidation in oxo acid production, the higher overall mass transfer rate associated with oxygen based liquid oxidation reactor technology increases the amount of oxygen available for reaction in the liquid phase and thereby reduces selectivity losses that are associated with oxygen starved conditions.

Furthermore, for a given aldehyde conversion rate, the overall higher mass transfer rate that is obtained with oxygen allows for operation at lower temperature and pressure than in conventional air base reaction systems. Since the gas phase oxygen concentration is much higher in an oxygen based system, the same oxygen partial pressure can be achieved at a much lower total pressure than with air. Also, since both temperature and oxygen concentration increases the reaction rate, a given reaction rate can be maintained by increasing the oxygen concentration and lowering the reaction temperature. Operation at such lower temperature further reduces byproduct formation and increases product selectivity.

An important advantage of the liquid oxidation reactor system is that it is a well mixed stirred tank reactor system having separate reaction and gas disengagement zones that are defined by the baffle means as disclosed in U.S. Pat. No. 4,900,480. Since said baffle or other means keeps most of the unreacted oxygen from disengaging from the liquid before it is reacted, very little inert gas is required to assure that the headspace gas is below the flammable limit, which with acceptable safety margins, is typically 5% oxygen or less.

As indicated above, it is convenient and generally desirable to use the liquid oxidation reactor system disclosed in U.S. Pat. No. 4,900,480, but that the other embodiments thereof can also be employed in the practice of this invention. Furthermore, while essentially pure oxygen, e.g., 99% pure oxygen, can be employed as the oxygen containing gas used for the oxidation of organic liquids such as aldehydes, lower purity oxygen can also be used for such purpose. Thus, oxygen containing gas having an oxygen concentration of about 50% by volume or above will offer improved selectivity over the use of feed air. The magnitude of the improved selectivity will generally increase in proportion to the oxygen concentration in the oxygen containing gas. In particular, oxygen of greater than 90% purity should generally result in nearly the same benefit as is obtained using 99% pure oxygen.

While oxygen may be used to advantage in a bubble column or gas lift bubble column reactors to improve performance relative to feed air in these reaction configurations due to the higher available oxygen, partial pressure, a large quantity of inert gas is necessary to inert the headspace in these reactors, rendering the use of such reactors less desirable than the practice of this invention. The benefits of oxygen can also be realized in other well mixed stirred tank reactor configurations. However, as in the bubble column approach, the amount of unreacted oxygen that escapes into the reactor headspace will be greater in non-liquid oxidation reactor stirred tank systems. Hence, the amount of inert gas required to maintain nonflammable conditions in the headspace is typically much greater than for liquid oxidation reactor operations. Processes using such non-liquid oxidation reactor stirred tanks systems are again economically unfavorable compared to the use of an liquid oxidation reactor approach because of the high cost of nitrogen or other inert purge gas and the higher costs associated with the removal of organic compounds from the purge gas prior to the discharge of said purge gas to the atmosphere.

The liquid oxidation reactor employs a shell and tube reactor configuration so as to achieve a high heat transfer surface to reactor volume ratio together with enhanced heat transfer due to forced circulation of the reaction liquid. Also, in the liquid oxidation reactor, means are provided to achieve gas circulation throughout the entire reaction volume, thereby improving reaction productivity and reaction selectivity.

The liquid oxidation reactor employed in this invention is particularly beneficial for reaction systems wherein the reactant gas can form a flammable gas mixture with the vapor above the reactant liquid, as in the oxygen based oxidation of organic chemicals. In such cases, the oxygen gas is sparged under the liquid surface directly into the impeller suction. A flammable gas mixture is formed at the point of gas injection. However, since the gas is dispersed within the liquid, it is not hazardous since flame cannot propagate through the liquid. The gas liquid dispersion is pumped down through the draft tube into the bottom mixing chamber and up through the heat exchanger tubes. The gas then disengages from the liquid phase and collects in the gas space above the liquid. This configuration takes advantage of beneficial heat transfer and fluid flow characteristics offered by the pumped shell and tube design since the reactant gas is circulated throughout the entire reactor volume. The productivity of the entire reactor volume is maximized, and the potential for reactant starved conditions that can occur is minimized.

In an embodiment, a vertical shell and tube heat exchange reactor has a hollow draft tube positioned in the center thereof. Impeller means are positioned within said draft tube, preferably at the upper portion, and are adapted to recirculate liquid downward through said draft tube into a bottom mixing chamber, and up through heat exchanger tubes. A liquid feed is passed through a feed line containing flow control means preferably into upper portion of the reactor. Cooling water is passed to the reactor through an inlet and is withdrawn through an outlet. The liquid is caused to rise to a liquid level in said upper portion, which is in fluid communication with an upper chamber comprising an overhead gas phase from which gas is vented through a gas discharge line containing a flow control means. Product is discharged from the bottom mixing chamber through a line containing flow control means. Liquid level control means is adapted to receive input signals as to liquid level and to send output signal to flow control means so as to maintain the desired liquid level. A drive motor is connected to drive shaft, adapted to drive impeller means. Upper baffle means and lower baffle means are provided to facilitate the desired recirculation of liquid downward in the draft tube and upward in said tubes.

In an embodiment, back pressure control means are provided to receive an input signal as to the pressure in upper chamber and to send an output signal to flow control means in a gas discharge line. In addition, an inert purge line containing normal flow control means, e.g. valve, is used to introduce a purge gas to the upper chamber or reactor above the liquid level. An oxygen analyzer is adapted to receive input signals as to the oxygen concentration in the upper chamber and to send output signals to emergency flow control means to enable additional quantities of inert purge gas to flow through emergency flow line to reactor or upper chamber above liquid level.

In flammable systems such as exist in this invention, the potential to form flammable gas mixtures in the waste gas stream must be eliminated. For example, in the oxidation of an organic liquid with air, the oxygen content in the waste gas must be reduced below the flammable oxygen concentration which is typically between 8% and 12%. In practice, the oxygen concentration is reduced to below 5% to provide an adequate safety margin. Nitrogen or other diluent gas can be added to the waste gas to reduce the oxygen concentration to less than 5%. If pure or nearly pure oxygen is used, the oxygen must be reacted away or an inert diluent is added to the waste gas, but the mass transfer performance of the system is improved due to the higher oxygen concentration.

Oxygen is used in the reactor system of the invention to improve selectivity in the oxidation of organic liquids to the corresponding organic acids. With oxygen, the partial pressure of oxygen in the oxygen containing gas bubbles within the oxidation reactor is significantly greater than the inherently limited oxygen partial pressure in air. Consequently, the driving force for mass transfer is greater, and the likelihood of oxygen starved conditions which cause byproduct formation is lower, with oxygen.

The liquid oxidation reactor useful in this invention is a well mixed stirred tank reactor system, consequently oxygen bubbles are uniformly distributed throughout the liquid. Thus, with said reactor there are no zones that are oxygen starved due to poor gas liquid contacting. Depending on the vapor pressure of the liquid which acts as a diluent, the average oxygen concentration in the gas bubbles is much higher than it is in a conventional reactor with air. In systems with a very low liquid vapor pressure, the average oxygen concentration can approach 95% or higher. This compares favorably to the average 5% oxygen concentration in a conventional air based stirred tank reactor and to the average of 13% in a bubble column reactor.

The overall higher mass transfer rate gives rise to improved oxygen mass transfer which increases the amount of oxygen available for reaction in the liquid phase and thereby reduces selectivity losses that are associated with oxygen starved conditions. The overall higher mass transfer rate also allows for operation at lower temperature further reduces byproduct formation and increases selectivity.

Illustrative liquid oxidation reactors (also referred as liquid organic reactors) and reaction equipment useful for conducting the oxidation step of the process of this invention are described, for example, in U.S. Pat. Nos. 5,451,348, 5,371,283, 5,108,662, 5,356,600, 5,200,080, 5,009,816, 4,919,849, 4,965,022, 4,867,918, 4,544,207 and 4,454,077 and European Patent Application Nos. EP 0 792 683 A2, EP 0 781 754 A1, EP 0 796 837 A1 and EP 0 792 865 A1, the disclosures of which are incorporated herein by reference.

The liquid oxidation reactor preferably has a reactor volume sufficient to take advantage of economies of scale, e.g., a reactor volume of at least about 500 gallons or less, preferably at least about 1000 gallons and more preferably at least about 2000 gallons or greater.

In a preferred embodiment of this invention, the liquid oxidation reactor comprises:

a) a vertically positioned tube and shell reactor vessel having a hollow draft tube in the center thereof and heat exchanger tubes in the annular space between the hollow draft tube and the outer wall of the reactor vessel, said reactor vessel having an upper space above and a hollow mixing chamber below said hollow draft tube and said heat exchanger tube;

b) impeller means positioned within said hollow draft tube and adapted to cause the rapid flow of the organic liquid downward through the hollow draft tube into the bottom mixing chamber and rapidly upward through said heat exchanger tubes as a substantially uniform dispersion and into said upper space in the reactor vessel;

c) an upper chamber positioned above and in fluid communication with said reactor vessel, said upper chamber having a vapor space above a desired liquid level;

d) at least one generally horizontal gas containment baffle disposed between said upper chamber and said reaction vessel in such a manner that the vapor space above the liquid level in said upper chamber is maintained below both the LOV and LFL, said gas containment baffle being formed with a central hole to enable said impeller means to extend generally concentrically through said hole in said gas containment baffle;

e) conduit means for introducing said organic liquid into the reactor vessel and for introducing said pure oxygen or oxygen-enriched air containing at least about 50% oxygen into said reactor vessel or the upper chamber for rapid recirculation with the organic liquid downward through the hollow draft tubes into the bottom mixing chamber and rapidly upward through said heat exchanger tubes into said upper space;

f) conduit means for withdrawing product liquid from the reactor vessel;

g) conduit means for flowing cooling fluid to the reactor vessel for the removal of exothermic heat of reaction generated within said reactor vessel; and h) control means for maintaining a desired liquid level within the reactor vessel or within the upper chamber.

In a more preferred embodiment, the liquid oxidation reactor further comprises at least one generally horizontal seal baffle disposed within the vapor space of said upper chamber in such a manner that the vapor space above said seal baffle is maintained below both the LOV and LFL, preferably under an inert atmosphere, said seal baffle being formed with a central hole to enable said impeller means to extend generally concentrically through said hole in said seal baffle.

Configuration of two or more liquid oxidation reactors in series, or an liquid oxidation reactor followed in series by a plug flow reactor, enables efficiency to be improved by increasing organic raw material conversion as described below.

The liquid oxidation reactor is a close approximation to a perfectly back-mixed gas-liquid reactor or continuous stirred tank reactor (CSTR). This means that the concentration of all components in the reaction zone is driven close to uniformity by turbulent mixing and rapid loop circulation.

As a consequence the particular organic, e.g., aldehyde, concentration in the liquid product, take-off will never be zero no matter how much reaction residence time is provided by increasing the reactor volume. Thus, while the CSTR mode ensures there are no regions which are starved of oxygen (which could cause undesired byproduct formation), operation of a single CSTR prevents the raw material (aldehyde) from being driven to complete conversion in the manner of a plug flow reactor where raw materials are progressively consumed to extinction throughout the length of a one directional reactor flow path.

The level of conversion can be increased in a CSTR by increasing the reactor volume, thereby increasing the residence time in the reactor. This is not always desirable since as the reactor size increases the reaction volume (and associated reaction heat release) increase faster than available heat transfer surface area, and the ability to maintain the reactor in a well mixed mode also becomes increasingly difficult.

Commercial CSTR processes can overcome the disadvantage of partial raw material conversion by separating the unconverted raw material from the product and recycling it to the reactor. This is not economic with processes in which an undesired byproduct is difficult to separate from the raw material since the byproducts would infinitely accumulate in a closed loop. C5 oxo acids are an example where a reaction byproduct (butyl formates) does not readily separate from the unconverted aldehyde. In these circumstances it is often desirable to configure several backmixed reactors in series, in effect to simulate a multi-staged plug flow reactor, and in this way drive the raw material to an economic level of conversion. This strategy also enables good control of byproduct generation by limiting interstage conversion and minimizing associated temperature rise.

The number of stages in a CSTR train is typically determined by trading the capital cost of multiple reactors against the level of raw material conversion achieved. When considering placing multiple liquid oxidation reactors in series another factor must be considered arising out of the free radical mechanism of oxidation processes. Such free radical mechanisms involve initiation, propagation and termination steps as exemplified above for aldehyde oxidation. When the concentration of raw material is high the rate of initiation and propagation is high relative to the rate of free radical termination. However when the raw material concentration is low, the rate of termination more closely matches the rate of initiation. This may cause a significant decrease in the observed rate of oxidation in the latter stages of a CSTR train.

With the liquid oxidation reactor, a level of organic liquid, e.g., aldehyde, conversion of 90–92% can be achieved at a residence time of about 1 hour in a single stage; this can be increased to an overall level of about 96–98% in a second similar stage. Beyond this the aldehyde reaction rates are very low and further stages are uneconomic unless the remaining aldehyde is concentrated by stripping away from the product acid.

Alternatively the raw material conversion can be improved by sequencing a plug flow reactor, such as a bubble column, in series after an liquid oxidation reactor. Adequate heat removal from bubble columns is difficult to achieve with highly exothermic reactions such as oxidations. By adjusting the duty on the bubble column so that it serves merely as a polishing reactor this problem can be avoided.

The process of this invention is useful for preparing substituted and unsubstituted organic acids in high purity. Illustrative preferred organic acids prepared by the oxidation process of this invention include, for example, formic acid, acetic acid, propionic acid, butyric acid, valeric acid, caproic acid, caprylic acid, capric acid, lauric acid, phenylacetic acid, benzoic acid, phthalic acid, isophthalic acid, terephthalic acid, adipic acid, 2-ethylhexanoic acid, isobutyric acid, 2-methylbutyric acid, 2-propylheptanoic acid, 2-phenylpropionic acid, 2-(p-isobutylphenyl)propionic acid, 2-(6-methoxy-2-naphthyl)propionic acid and the like. Illustrative of suitable organic acids which can be prepared by the processes of this invention include those permissible organic acids which are described in Kirk-Othmer, Encyclopedia of Chemical Technology, Third Edition, 1984, the pertinent portions of which are incorporated herein by reference.

Preferred organic acids include carboxylic acids prepared from the oxidation of oxo aldehydes, e.g., valeric acid, 2-ethylhexanoic acid, 2-propylheptanoic acid and the like. Such carboxylic acids prepared from oxo aldehydes are referred to herein as "oxo acids".

In accordance with this invention, the crude reaction product fluid is refined to give said one or more organic acids in high purity, i.e., an organic acid purity of at least about 95 percent, preferably at least about 97 percent, and more preferably at least about 99 percent or greater. Suitable refining methods include, for example, distillation, solvent extraction, crystallization, vaporization, phase separation, filtration and the like, including combinations thereof. Distillation is the preferred refining method for use in this invention. The refining can be conducted in a single separation zone or in a plurality of separation zones. This invention is not intended to be limited in any manner with respect to the permissible refining methods.

The organic acids described herein is useful in a variety of applications, such as intermediates in the manufacture of chemical compounds, pharmaceutical manufacture and the like.

For purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxy, hydroxyalkyl, amino, aminoalkyl, halogen and the like in which the number of carbons can range from 1 to about 20 or more, preferably from 1 to about 12. The permissible substituents can be one or more and the same or different for appropriate organic compounds. This invention is not intended to be limited in any manner by the permissible substituents of organic compounds.

Certain of the following examples are provided to further illustrate this invention.

EXAMPLE 1

Valeraldehyde oxidation with pure oxygen was conducted in a liquid oxidation reactor at a rate of 7 gmol/lit/hr. The reaction zone temperature was operated at a set point of 65° C. A nitrogen flow of 150 scfm was purged through the vapor space above the liquid level. Coolant was fed to the shell of the reactor to remove the heat of reaction. The reaction temperature was observed to oscillate approximately ±1.75° C. around 65° C., each oscillation cycle occurring over a time period of approximately 3 minutes. During the downward temperature phase of the oscillation, the oxygen concentration in the vapor space was observed to rise from a mean value of 0.8 mol % to approximately 3.7 mol %. The reactor was equipped with an automatic shut down level at 4 mol % to protect the vapor space from approaching the LOV. If the downward temperature cycle reduced the temperature from 65 to 63° C., the oxygen concentration exceeded 4 mol % and the reactor feeds were shut off.

EXAMPLE 2

In a manner similar to Example 1, valeraldehyde oxidation was conducted, however, temperature oscillation was restricted to ±1° C. of a set point of 65° C. Oxygen concentration in the vapor space rose from an initial value of 0.8 mol % to a maximum value of 2.5 mol % during the down ward temperature cycle. Continuous operation of the reactor under the shut down level of 4 mol % oxygen was maintained.

EXAMPLE 3

Valeraldehyde oxidation to valeric acid was conducted in a liquid oxidation reactor using pure oxygen and the crude product was refined in a conventional distillation scheme. The amounts of the decarbonylation byproducts, i.e., butyraldehyde and butanol, in the crude are compared in FIG. 5 for the oxygen based liquid oxidation reactor and an air based reactor. During refining butyraldehyde can undergo further reaction to produce butyric acid and butanol can esterify with valeric acid to produce butyl valerate. The amounts of butyric acid and butyl valerate remaining in the refined valeric acid product after processing in similar refining operations are also shown in FIG. 5 for the oxygen based liquid oxidation reactor product and an air reactor.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for producing one or more organic acids in high purity which process comprises (i) oxidizing in a liquid oxidation reactor one or more organic liquids with essentially pure oxygen or oxygen-enriched air containing at least about 50% oxygen, at a temperature sufficiently stable to prevent cycling of reaction rate, wherein said temperature is controlled to within about ±3° C. of a target temperature, to produce a crude reaction product fluid, and (ii) refining said crude reaction product fluid to give said one or more organic acids in high purity.

2. A process for producing one or more organic acids in high purity which process comprises (i) oxidizing in a liquid oxidation reactor one or more organic liquids with essentially pure oxygen or oxygen-enrich d air containing at least about 50% oxygen, at a temperature sufficiently stable to prevent cycling of reaction rate, wherein said temperature is controlled to within about ±3° C. of a target temperature, to produce a crude reaction product fluid, and (ii) refining said crude reaction product fluid to give said one or more organic acids in high purity; wherein said liquid oxidation reactor comprises:

a) a vertically positioned tube and shell reactor vessel having a hollow draft tube in the center thereof and heat exchanger tubes in the annular space between the hollow draft tube and the outer wall of the reactor vessel, said reactor vessel having an upper space above and a hollow mixing chamber below said hollow draft tube and said heat exchanger tubes;

b) impeller means positioned within said hollow draft tube and adapted to cause the rapid flow of the organic liquid downward through the hollow draft tube into the bottom mixing chamber and rapidly upward through said heat exchanger tubes as a substantially uniform dispersion and into said upper space in the reactor vessel;

c) an upper chamber positioned above and in fluid communication with said reactor vessel, said upper chamber having a vapor space above a desired liquid level;

d) at least one generally horizontal gas containment baffle disposed between said upper chamber and said reaction vessel in such a manner that the vapor space above the liquid level in said upper chamber is maintained below both the LOV and LFL, said gas containment baffle being formed with a central hole to enable said impeller means to extend generally concentrically through said hole in said gas containment baffle;

e) at least one generally horizontal seal baffle disposed within the vapor space of said upper chamber in such a manner that the vapor space above said seal baffle is maintained under an inert atmosphere, said seal baffle being formed with a central hole to enable said impeller means to extend generally concentrically through said hole in said seal baffle;

f) conduit means for introducing said organic liquid into the reactor vessel and for introducing said pure oxygen or oxygen-enriched air containing at least about 50% oxygen into said reactor vessel or the upper chamber for rapid recirculation with the organic liquid downward through the hollow draft tubes into the bottom mixing chamber and rapidly upward through said heat exchanger tubes into said upper space;

g) conduit means for withdrawing product liquid from the reactor vessel;

h) conduit means for flowing cooling fluid to the reactor vessel for the removal of exothermic heat of reaction generated within said reactor vessel; and i) control means for maintaining a desired liquid level within the reactor vessel or within the upper chamber.

3. A process for producing one or more organic acids in high purity which process comprises (i) oxidizing in a primary liquid oxidation reactor one or more organic liquids with essentially pure oxygen or oxygen-enriched air containing at least about 50% oxygen, at a temperature sufficiently stable to prevent cycling of reaction rate, wherein said temperature is within ±3° C. of a target temperature, to produce a first crude reaction product fluid, (ii) removing said first crude reaction product fluid from said primary liquid oxidation reactor, (iii) feeding said first crude reaction product fluid to at least one secondary liquid oxidation reactor or plug flow reactor, (iv) oxidizing in said secondary liquid oxidation reactor or plug flow reactor said first crude reaction product fluid with essentially pure oxygen or oxygen-enriched air containing at least about 50% oxygen to product a second crude reaction product fluid, and (v) refining said second crude reaction product fluid to give said one or more organic acids in high purity; wherein said primary liquid oxidation reactor, and optionally said secondary liquid oxidation reactor comprise:

a) a vertically positioned tube and shell reactor vessel having a hollow draft tube in the center thereof and heat exchanger tubes in the annular space between the hollow draft tube and the outer wall of the reactor vessel, said reactor vessel having an upper space above and a hollow mixing chamber below said hollow draft tube and said heat exchanger tubes;

b) impeller means positioned within said hollow draft tube and adapted to cause the rapid flow of the organic liquid downward through the hollow draft tube into the bottom mixing chamber and rapidly upward through said heat exchanger tubes as a substantially uniform dispersion and into said upper space in the reactor vessel;

c) an upper chamber positioned above and in fluid communication with said reactor vessel, said upper chamber having a vapor space above a desired liquid level;

d) at least one generally horizontal gas containment baffle disposed between said upper chamber and said reaction vessel in such a manner that the vapor space above the liquid level in said upper chamber is maintained below both the LOV and LFL, said gas containment baffle being formed with a central hole to enable said impeller means to extend generally concentrically through said hole in said gas containment baffle;

e) at least one generally horizontal seal baffle disposed within the vapor space of said upper chamber in such a manner that the vapor space above said seal baffle is maintained under an inert atmosphere, said seal baffle being formed with a central hole to enable said impeller means to extend generally concentrically through said hole in said seal baffle;

f) conduit means for introducing said organic liquid into the reactor vessel and for introducing said pure oxygen or oxygen-enriched air containing at least about 50% oxygen into said reactor vessel or the upper chamber for rapid recirculation with the organic liquid downward through the hollow draft tubes into the bottom mixing chamber and rapidly upward through said heat exchanger tubes into said upper space;

g) conduit means for withdrawing product liquid from the reactor vessel;

h) conduit means for flowing cooling fluid to the reactor vessel for the removal of exothermic heat of reaction generated within said reactor vessel; and i) control means for maintaining a desired liquid level within the reactor vessel or within the upper chamber.

4. The process of claim 2 wherein said target temperature is selected from an individual temperature in the range of from about −25° C. or lower to about 125° C.

5. The process of claim 2 wherein a temperature upset will not cause the release of amounts of oxygen to the vapor space of said liquid oxidation reactor which may cause the vapor region to exceed LOV or LFL.

6. The process of claim 2 wherein forced circulation of said organic liquid and pure oxygen or oxygen-enriched air containing at least about 50% oxygen rapidly throughout the reactor system enhances heat and mass transfer between said organic liquid and pure oxygen or oxygen-enriched air containing at least about 50% oxygen, thereby maximizing volumetric reactor productivity and improving desired product selectivity.

7. The process of claim 3 wherein two or more liquid oxidation reactors are configured in series.

8. The process of claim 3 wherein a liquid oxidation reactor and a plug flow reactor are configured in series.

9. The process of claim 2 wherein said organic liquid comprises one or more aldehydes, alcohols, alkylbenzenes or cyclic aliphatic hydrocarbons.

10. The process of claim 9 wherein said organic liquid comprises one or more aldehydes selected from formaldehyde, acetaldehyde, propionaldehyde, n-butyraldehyde, 2-methylbutyraldehyde, iso-butyraldehyde, n-valeraldehyde, caproaldehyde, heptaldehyde, nonylaldehyde, phenylacetaldehyde, benzaldehyde, o-tolualdehyde, m-tolualdehyde, p-tolualdehyde, salicylaldehyde, p-hydroxybenzaldehyde, anisaldehyde, vanillin, piperonal, 2-ethylhexaldehyde, 2-propylheptaldehyde, 2-phenylpropionaldehyde, 2-[p-isobutylphenyl]propionaldehyde, and 2-[6-methoxy-2-naphthyl]propionaldehyde.

11. The process of claim 9 wherein said organic liquid comprises one or more alcohols selected from 2-ethylhexanol, 2-propylheptanol, isobutyl alcohol, and 2-methyl-1-butanol.

12. The process of claim 2 wherein said organic liquid comprises one or more alkylbenzenes selected from p-nitrotoluene, o-bromotoluene, ethylbenzene, n-butylbenzene, m-xylene, p-xylene, and toluene.

13. The process of claim 2 wherein said organic liquid comprises one or more cyclic aliphatic hydrocarbons selected from cyclohexane, cyclooctane, cycloheptane, and methylcyclohexane.

14. The process of claim 2 herein said organic acid comprises on or more of formic acid, acetic acid, propionic acid, butyric acid, valeric acid, caproic acid, caprylic acid, capric acid, lauric acid, phenylacetic acid, benzoic acid, phthalic acid, isophthalic acid, terephthalic acid, adipic acid, 2-ethylhexanoic acid, isobutyric acid, 2-methylbutyric acid, 2-propylheptanoic acid, 2-phenylpropionic acid, 2-(p-isobutylphenyl)propionic acid, and 2-(6-methoxy-2-naphthyl) propionic acid.

15. The process of claim 2 wherein said organic liquid comprises an oxo aldehyde and said organic acid comprises an oxo acid.

16. The process of claim 2 wherein said oxidizing has an activation energy of greater than about 15 kcal/mol and an exothermic heat of reaction of greater than about 100,000 BTU/lb-mol.

* * * * *